United States Patent
Monbouquette et al.

(10) Patent No.: US 9,428,806 B2
(45) Date of Patent: Aug. 30, 2016

(54) APPARATUS AND METHOD FOR ELECTRICAL DETECTION OF OLIGONUCLEOTIDES THROUGH PORE BLOCKADES

(71) Applicant: THE REGENTS OF THE UNIVERSITY OF CALIFORNIA, Oakland, CA (US)

(72) Inventors: Harold G. Monbouquette, Santa Monica, CA (US); Jacob J. Schmidt, Sherman Oaks, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/188,956

(22) Filed: Feb. 25, 2014

(65) Prior Publication Data

US 2014/0248711 A1  Sep. 4, 2014

Related U.S. Application Data

(63) Continuation of application No. PCT/US2012/053540, filed on Aug. 31, 2012.

(60) Provisional application No. 61/530,349, filed on Sep. 1, 2011.

(51) Int. Cl.
*C12Q 1/68* (2006.01)
*G01N 33/487* (2006.01)

(52) U.S. Cl.
CPC ....... *C12Q 1/6869* (2013.01); *G01N 33/48721* (2013.01)

(58) Field of Classification Search
CPC .................. C12Q 1/6869; G01N 33/48721
USPC ........................................ 435/6.1; 422/82.01
See application file for complete search history.

(56) References Cited

U.S. PATENT DOCUMENTS

| | | | |
|---|---|---|---|
| 5,356,776 A * | 10/1994 | Kambara | C12Q 1/68 204/461 |
| 5,789,167 A | 8/1998 | Konrad | |
| 6,129,828 A | 10/2000 | Sheldon, III et al. | |
| 6,391,558 B1 | 5/2002 | Henkens et al. | |
| 2005/0136408 A1 * | 6/2005 | Tom-Moy et al. | 435/6 |
| 2005/0287589 A1 | 12/2005 | Connolly | |
| 2006/0183112 A1 * | 8/2006 | Min et al. | 435/5 |
| 2007/0042366 A1 * | 2/2007 | Ling | 435/6 |
| 2007/0111202 A1 | 5/2007 | Henkens et al. | |
| 2009/0065372 A1 | 3/2009 | Marchal et al. | |
| 2009/0169431 A1 | 7/2009 | Kim et al. | |
| 2010/0267011 A1 * | 10/2010 | Kim et al. | 435/6 |

(Continued)

OTHER PUBLICATIONS

Karhanet et al "Single DNA molecule detection using nanopipettes and nanoparticles" Nano Letters, 2005, 5(2):403-407.*

(Continued)

*Primary Examiner* — Betty Forman
(74) *Attorney, Agent, or Firm* — O'Banion & Ritchey LLP; John P. O'Banion

(57) ABSTRACT

Systems and methods for specific nucleic acid (NA) sequence detection that do not rely on polymerase chain reaction (PCR) for target sequence amplification and do not require any special reagents other than a complementary sequence capture probe conjugated to spherical beads.

12 Claims, 11 Drawing Sheets

(56) References Cited

U.S. PATENT DOCUMENTS

2011/0308950 A1* 12/2011 Sakai et al. .................. 204/452
2012/0312083 A1* 12/2012 Akahori et al. ............. 73/61.72

OTHER PUBLICATIONS

Korean Intellectual Property Office, International Search Report and Written Opinion, issued on Feb. 25, 2013 for corresponding International Patent Application No. PCT/US2012/053540 (pp. 1-13) and Claims Searched (pp. 14-20). pp. 1-20.

Singer, A. et al., "Nanopore based sequence specific detection of duplex DNA for genomic profiling," Nano Letters, Jan. 20, 2010, vol. 10, No. 2, pp. 738-742.

Kim, Y.R., et al., "Nanopore sensor for fast label-free detection of short double-stranded DNAs," Biosensors and Bioelectronics, Jan. 10, 2007, vol. 22, No. 12, pp. 2926-2931.

Kim, M.J., et al., "Rapid fabrication of uniformly sized nanopores and nanopore arrays for parallel DNA analysis," Advanced Materials, Nov. 27, 2006, vol. 18, Issue 23, pp. 3149-3153.

Esfandiari, L. et al., "Sequence-specific nucleic acid detection from binary pore conductance measurement," Journal of the American Chemical Society, Aug. 29, 2012, vol. 134, No. 38, pp. 15880-15886.

Daniels and Pourmand, "Label-Free Impedance Biosensors: Opportunities and Challenges," Electroanalysis 19, 2007, No. 12, 1239-1257 (pp. 1-19).

Drummond, et al., "Electrochemical DNA sensors," Nature Biotechnology, Sep. 30, 2013, vol. 21, No. 10, pp. 1192-1199 (pp. 1-8).

Barbaro, et al. "A CMOS, Fully Integrated Sensor for Electronic Detection of DNA Hybridization," IEEE Electron Device Letters, vol. 27, No. 7, Jul. 2006.

* cited by examiner

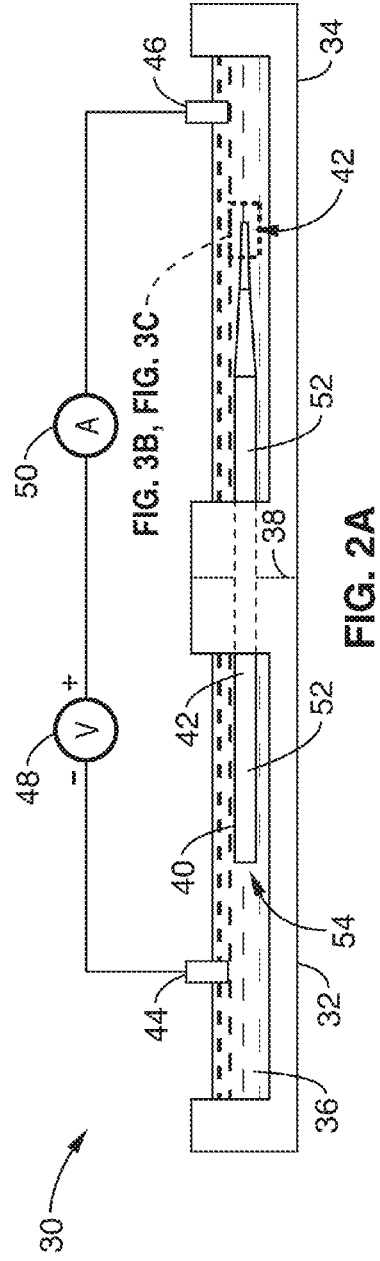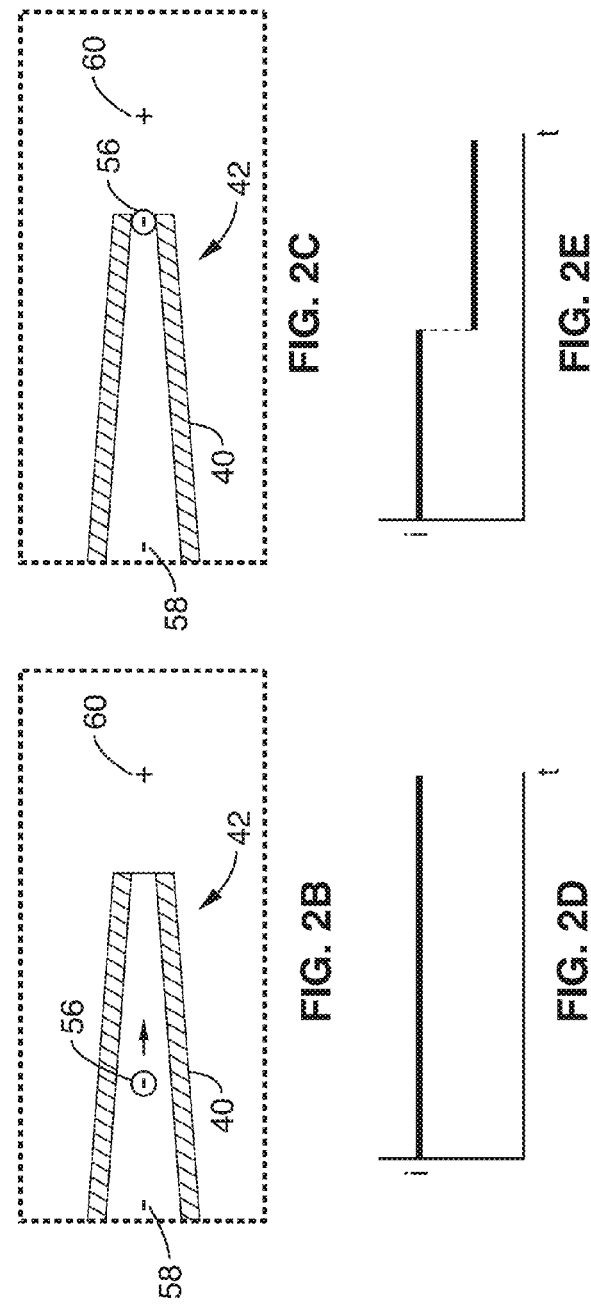

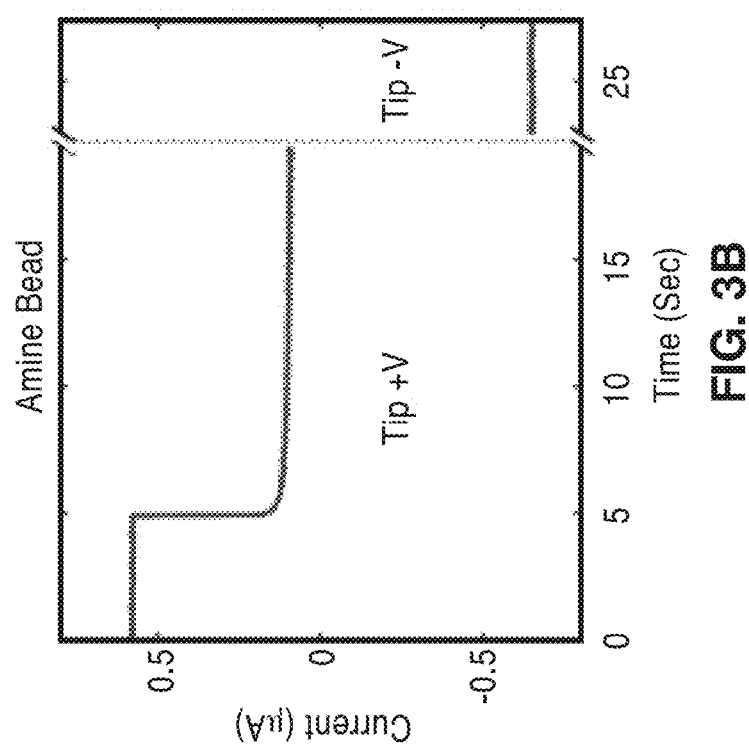
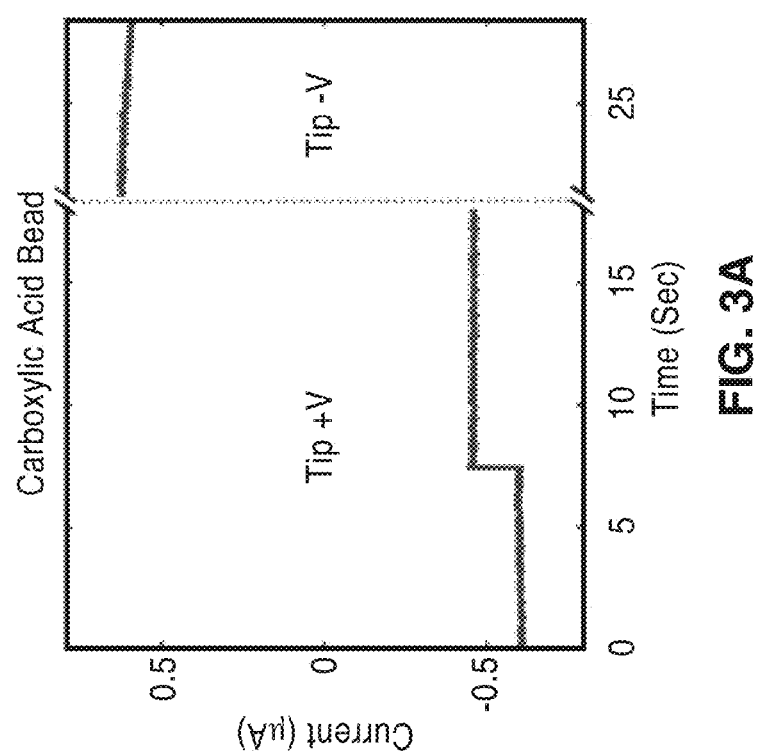
FIG. 3B
FIG. 3A

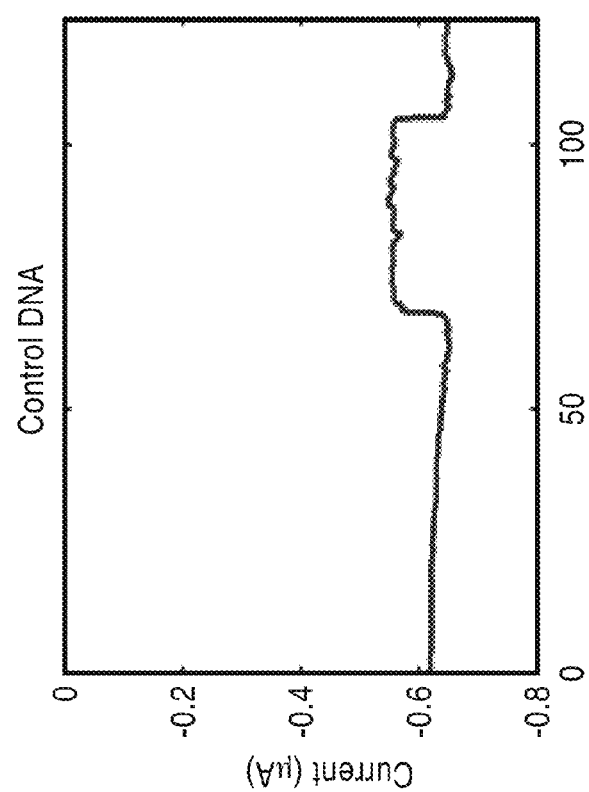
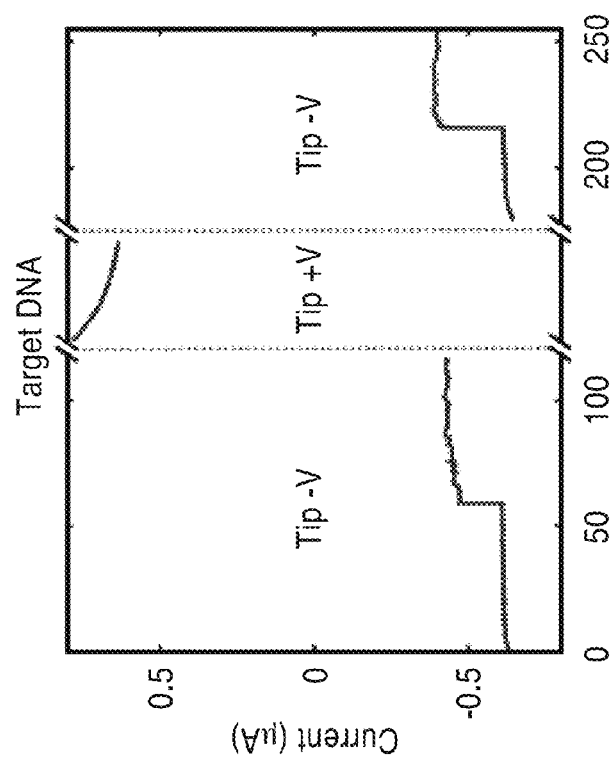

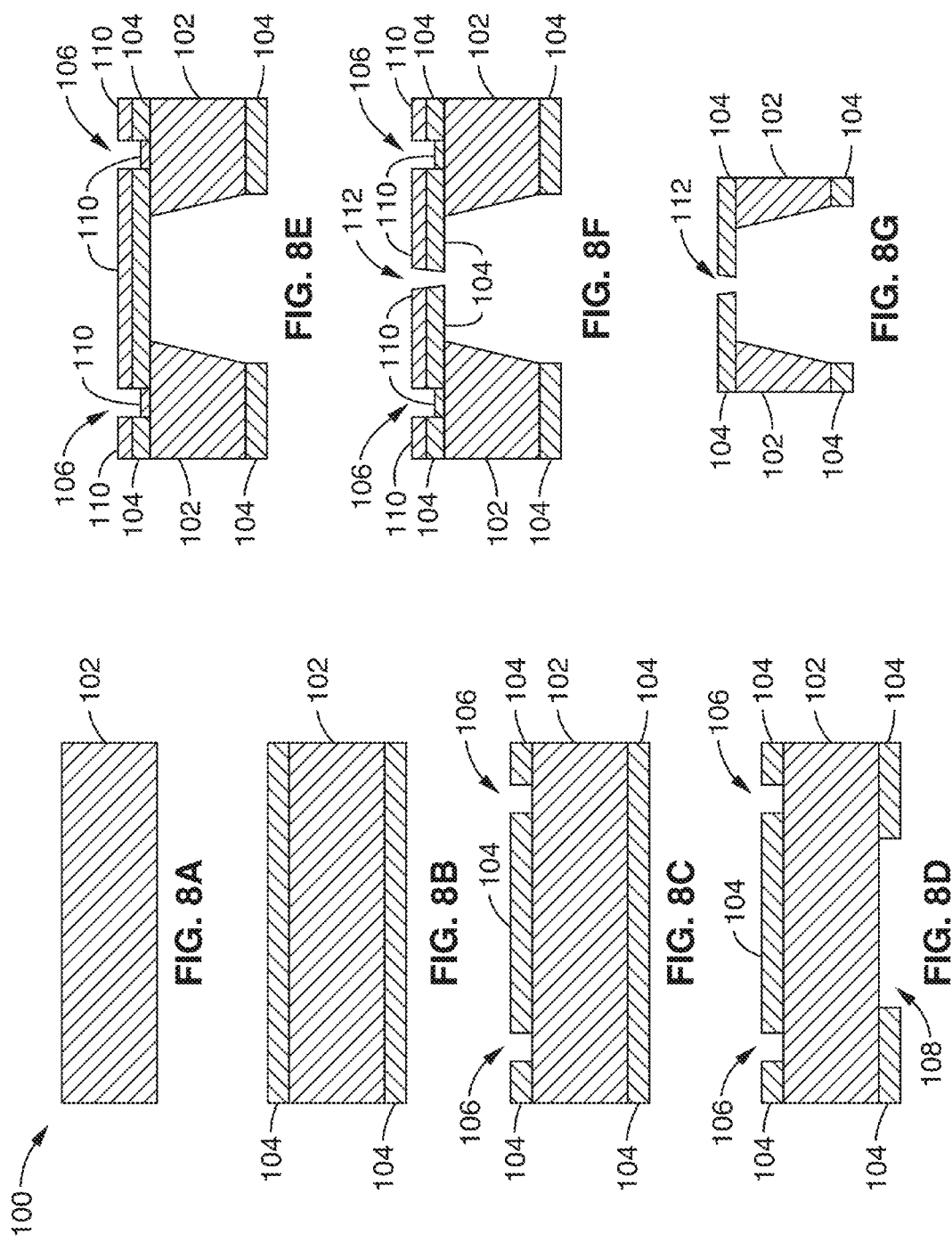

APPARATUS AND METHOD FOR ELECTRICAL DETECTION OF OLIGONUCLEOTIDES THROUGH PORE BLOCKADES

CROSS-REFERENCE TO RELATED APPLICATIONS

This application is a 35 U.S.C. §111(a) continuation of PCT international application number PCT/US2012/053540 filed on Aug. 31, 2012, incorporated herein by reference in its entirety, which claims the benefit of U.S. provisional patent application Ser. No. 61/530,349 filed on Sep. 1, 2011, incorporated herein by reference in its entirety. Priority is claimed to each of the foregoing applications.

The above-referenced PCT international application was published as PCT International Publication No. WO 2013/033647 on Mar. 7, 2013 and republished on May 10, 2013, which publications are incorporated herein by reference in their entireties.

This invention was made with Government support under HG006157, awarded by the National Institutes of Health. The Government has certain rights in the invention.

STATEMENT REGARDING FEDERALLY SPONSORED RESEARCH OR DEVELOPMENT

Not Applicable

INCORPORATION-BY-REFERENCE OF MATERIAL SUBMITTED IN A COMPUTER PROGRAM APPENDIX

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to the detection of specific nucleic acid (NA) sequences.

2. Description of Related Art

Conventional methods of detecting specific nucleic acid (NA) sequences often utilize fluorescent labels requiring optics for readout or amplification using polymerase chain reaction (PCR), both of which require a somewhat costly and bulky apparatus. There are many assays for sequence-specific DNA detection. Most of them are optical (e.g., microarrays, hairpins conjugated to quenched fluorophores, etc.) or enzyme-based (e.g., restriction fragment length polymorphism and a number of techniques utilizing PCR) and can even include mass spectrometry. Although services utilizing these techniques are offered commercially by a number of sources, the cost for a single specific assay can be somewhat high; the per assay cost can be reduced by running a larger number of assays in parallel.

BRIEF SUMMARY OF THE INVENTION

The present invention provides for specific nucleic acid (NA) sequence detection that does not rely on polymerase chain reaction (PCR) for target sequence amplification and does not require any special reagents other than a complementary sequence capture probe conjugated to spherical beads. According to an aspect of the invention, an apparatus for sequence-specific nucleic acid detection in a sample comprises a first chamber; a second chamber; a membrane separating the first and second chambers, the membrane having a pore extending through the membrane between the first and second chambers; a first electrode disposed in the first chamber; and a second electrode disposed in the second chamber. When a liquid is introduced into said first and second chambers, wherein when a source of direct electric current is connected to said electrodes with a negative polarity being connected to the first electrode, and wherein when a bead which is conjugated with a strand of capture probe nucleic acid that is complementary to a desired target sequence to be detected is subsequently introduced into the liquid in the first chamber, the presence of said target nucleic acid is indicated by a decrease in electric current between the electrodes in relation to electric current between the electrodes prior to introduction of the beads into the first chamber, said decrease in electric current resulting from movement of the bead and the bead causing blockage of the pore.

According to another aspect of the invention, A method for detecting the presence of nucleic acids with a target sequence from a sample, the method comprising: providing a detection apparatus, said detection apparatus comprising: a first chamber; a second chamber; a membrane separating said first and second chambers, said membrane having a pore extending through the membrane between the first and second chambers; a first electrode disposed in the first chamber; and a second electrode disposed in the second chamber; introducing a liquid into said first and second chambers; applying a direct electric current to said first and second electrodes with a negative polarity being connected to the first electrode; measuring electric current between the electrodes as a reference current; introducing, into said first chamber, a bead which is conjugated with one or more strands of capture probe nucleic acid that are complementary to a desired target sequence to be detected; and measuring electric current between the electrodes after introduction of the bead, wherein a decrease in measured electric current indicates the presence of one or more strands of target nucleic acid that are complimentary to the probe sequence conjugated to the bead.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 2A through FIG. 2C are cross-sectional diagrams showing an embodiment of the invention where a pipette is used as a tapered pore.

FIG. 2D and FIG. 2E are graphs showing the relationship of current over time for an unblocked pore and blocked pore, respectively, in relation to FIG. 2B and FIG. 2C, respectively.

FIG. 3A is a graph of an ionic current drop caused by pore blockade from a carboxylic acid-functionalized bead according to an embodiment of the invention.

FIG. 3B is a graph of an ionic current drop caused by pore blockade from an amine-functionalized bead according to an embodiment of the invention.

FIG. 5A is a graph of the permanent ionic current drop caused by beads incubated with target anthrax ssDNA, according to an embodiment of the invention.

FIG. 5B is a graph of the transient ionic current drops that were seen occasionally with beads incubated with control ssDNA, according to an embodiment of the invention.

FIG. 8A through FIG. 8G are diagrams, illustrating in cross section, an embodiment of a process for fabricating a detection chip according to an embodiment of the invention (not to scale).

DETAILED DESCRIPTION OF THE INVENTION

Figure 1B:
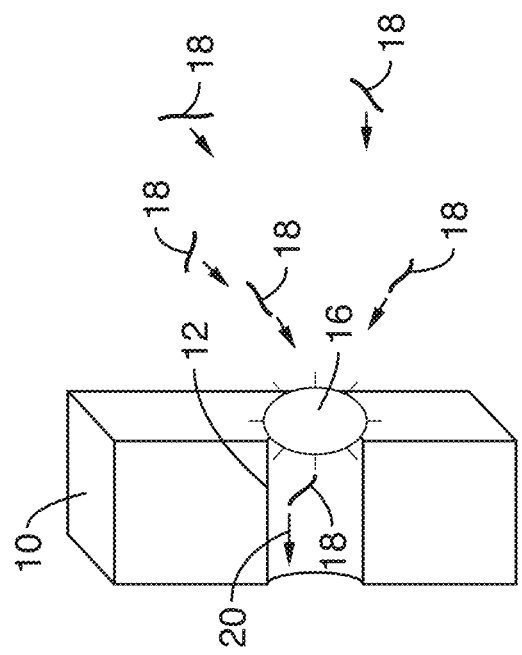
FIG. 1A and FIG. 1B are diagrams that schematically illustrate detection of oglionucleotides through pore blockade according to an embodiment of the invention.

In general terms, systems and methods according to embodiment of our invention provide for detection of sequence-specific nucleic acids by measuring a change in electrical current resulting from movement of conjugated beads in a first chamber toward a second chamber. The two chambers contain a liquid and are separated by a membrane having a pore therethrough. Each chamber has an electrode that is connected to a direct current source such that the electrode in the first chamber is a negative electrode and the electrode in the second chamber is a positive electrode. The presence of target nucleic acid that is complementary to a capture probe sequence results in hybridization of the target NA to the bead and bead movement causing a blockage of the pore. Pore blockage in turn causes a decrease in electrical current. In this way, hybridization of specific NA targets to complementary NA probe-bead conjugates generates an easily detected on/off current.

By way of example, and not of limitation, a detection apparatus according to an embodiment of the present invention includes a peptide nucleic acid (PNA) capture probe conjugated to spherical beads. PNA oligomers are uncharged analogs to DNA and RNA that share the same base chemistry and hybridize strongly to complementary NA sequences. Since the bead-PNA conjugates carry little or no charge, they do not exhibit electrophoretic movement in response to a steady, direct current (DC) electric field imposed through a pore. However, the substantial negative charge acquired upon capture of a target DNA or RNA sequence makes the hybridized conjugate electrophoretically mobile. If the pore size is smaller than or tapers to a diameter smaller than the bead diameter, the charged conjugate carrying the hybridized PNA and target NA would be expected to block the pore, create a blockade, and significantly increase its resistance, thereby causing a very strong, sustained drop in measured current. In such a way, this apparatus gives an essentially binary response signaling the absence or presence of a target NA. Accordingly, the present invention would be useful for applications where determination of the presence or absence of NA of a particular sequence is of primary concern such as in patient screening during epidemics, oncological status assessment during surgery, detection of food contaminants, and biowarfare agent detection.

Our inventive method for detection of specific NA sequences provides for a strong on/off signal in the presence of/absence of target NA. Previous work with molecular sensing using nanopores has focused on stochastic sensing of analyte concentration using natural or synthetic pores on the order of the molecular size. The use of such small nanopores is necessary to obtain measurable signal transients when single analytes traverse the pore. In contrast, the present invention recognizes that in many cases NA sequence detection, e.g., a simple yes/no response like that obtained with a pregnancy test kit, is of interest. In one embodiment of the invention, an essentially binary system response is obtained by selectively capturing the NA analyte with a relatively large particle that can subsequently block a pore thereby giving an orders of magnitude change in trans-pore current.

In one embodiment, spherical beads are conjugated with uncharged PNA capture probes. Using a standard oligonucleotide capture probe is potentially problematic, since that oligo will also have a negative charge, thereby rendering the bead conjugates electrophoretically mobile independent of the presence of the target NA. In contrast, and according to an embodiment of our invention, these bead-PNA conjugates are engineered to carry little or no surface charge. Thus, hybridization of target NA will result in addition of significant negative charge to this large particle. Electrophoresis of the now negatively charged bead-PNA-NA construct to a pore of diameter less than the bead diameter or tapered to a lesser diameter will lead to a large and stable blockade of that pore. The coupling of target NA to the PNA-bead conjugate thereby leads to an electromechanical amplification phenomenon that gives rise to a large, easily detected, binary modulation of electrical current. If sample NA is not complementary to the PNA capture probe on the bead and does not hybridize to it, the bead-PNA conjugates will not move in response to the field.

Figure 1A:
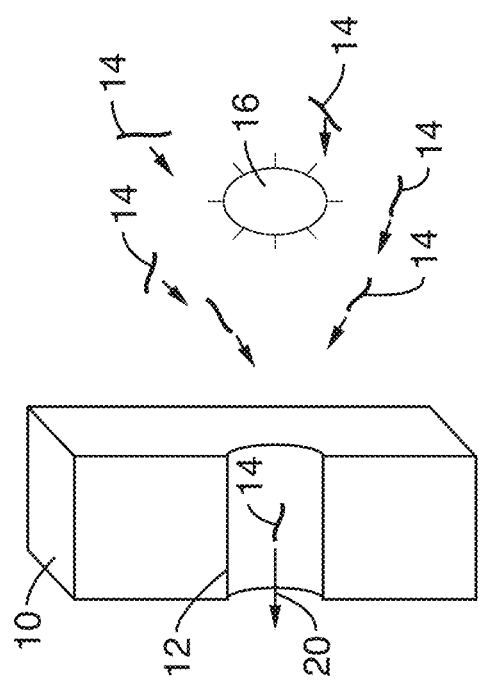

FIG. 1A and FIG. 1B schematically illustrate the inventive approach where, for example, a chip 10 containing a pore 12 is used as the membrane. FIG. 1A shows that, in the presence of non-complementary NA 14, the unbound PNA bead 16 is neutral and not electrophoretically mobile in the presence of a direct (DC) field. On the other hand, the charged non-hybridized NA 14 will move easily and quickly, passing through the pore 12 but with no significant change in the measured current. FIG. 1B shows the charged complementary NA 18 binding to the PNA bead 16, giving the bead mobility in the DC field that draws it to the pore 12, where it makes a lasting blockade of the transport current 20. In both cases, unbound NA traverses the pore, resulting only in very small transient current deflections.

The large size of the pore and its almost total occlusion by a bead carrying hybridized PNA-NA significantly increases the resultant signal and greatly simplifies the measurement electronics required. For example, in 1M KCl, the open pore current of αHL is ~100 pA for 100 mV applied potential, and the current that is sensed when DNA is present in the pore is ~20 pA; whereas a 100 nm diameter pore 100 nm long has an open pore current of 785 nA for the same applied potential. Easily measured current changes upon pore blockade by a bead-PNA conjugate with captured target NA thereby produce a strong, essentially binary signal that can be reported with simple circuitry and a low-power LED, for example.

Our invention exploits the highly specific nature of the binding between the target NA and the PNA capture probe conjugated to a bead to effectively increase the size of the target DNA molecule by orders of magnitude, making it much easier to detect. For target NA molecules of any significant size, the charge on the bead-PNA conjugate with hybridized NA will be great enough to affect its electrophoretic transport even for single molecule attachment events, potentially giving this technique the ultimate in sensitivity (i.e., femtomolar or lower). Single-digit femtomolar detection would require a signal within a reasonable time frame for the case where only one or a few target NA molecules are present in the sample. Femtomolar detection with our system is achievable with the incorporation of a system for microfluidic mixing in the sample reservoir and/or a scheme for electrokinetic concentration of the negatively charged bead-PNA carrying NA target in the proximity of the pore mouth. Of course, as the NA analyte concentration decreases, the hybridization time of the target molecule with the bead conjugate will increase as a result of mass transfer and capture kinetics. This can be addressed by using many PNA-bead conjugates; in the limit of low target concentration, even though many beads will contain no target molecules, they will also be immobile and undetectable.

In the event that electro-osmotic flow opposing the electrophoretic movement of NA hybridized bead-PNA conjugates into pores that are machined in silica or Si, the negative fixed charges present on silica surfaces or on the SiO2 layer on Si may have associated positive counterions whose electric field-induced flux can give rise to a convective, electro-osmotic flow. This flow could cause a significant Stokes drag force that prevents pore blockage by bead-PNA conjugates carrying hybridized NA. Such electro-osmotic flow can be suppressed through appropriate silanization of the pore walls as has been done in the glass capillaries used in capillary electrophoresis.

An embodiment of the present invention generally comprises a device capable of detecting in a sample the presence of specific sequences of DNA or RNA with high sensitivity and specificity. Such detection is commonly desired to identify, for example, the presence and type of known pathogens as well as single nucleotide polymorphisms which predispose or cause a number of diseases. The device is simple, compact, and modular and could find application in a wide range of settings, including clinical laboratories or field tests. It should be straightforward to incorporate the invention into compact, low power microfluidic devices. The device enables the detection of specific nucleic acid (NA) sequences by binding them with high specificity to spherical beads on which complementary sequences of oligonucleotides are covalently attached. The binding status of these beads can be easily and clearly detected electrically with simple electronics and results in a simple "YES" or "NO" signal, as is desired. The apparatus forming this device is quite simple and compact, with little fluid handling and minimal electrical circuitry required, resulting in simpler and lower cost use. The fluidic portion of the device can be separate from the detection and readout elements, enabling disposable modular cartridges capable of detecting many different sequences to be easily interchanged in the device, resulting in a general platform.

In one embodiment, the apparatus preferably utilizes a membrane containing one or more monodisperse pores of standard size, although a glass micropipette drawn to give an opening at the tip of controllable dimension also can be used as the "pore." An aqueous electrolyte solution surrounds the membrane on both sides. On one side of the pores in the solution are a small number of beads of size greater than the diameter of the pores. On these beads are covalently attached one or more molecules of single-stranded probe NAs of a sequence complementary to the target NA sequence to be detected. The NA sample solution to be sensed is mixed with the bead-containing solution on one side of the membrane. If the target NA of interest is present in this solution, it will bind to the bead-NA conjugate and these beads will thus acquire a significant increase in negative charge.

Placement of electrodes into the solutions on each side of the pore and application of a voltage between them will set up an electric field in the solution and therefore provide an electrophoretic force to the beads. If the electrode in the solution containing the beads is at a lower potential (i.e., more negative) than the other electrode, the negatively charged species in the bead-containing solution will move toward the pore. Since the diameter of the pores is specified to be large relative to atomic and molecular species, all of this material except the beads (e.g., unbound NA) can easily travel through the membrane pores to the other side. The system is designed such that beads with unbound target NA will not be transported efficiently to the pores, as will the beads with captured target NA that have acquired substantially more negative charge. The bead-NA conjugates with bound target NA will move to the mouths of the smaller diameter pores, but cannot fit through and will stay stuck at their entrance or wedged in a tapered pore with a smaller distal opening.

As this voltage is applied by the electrodes, the resultant current between the electrodes can also be measured. This current flows from one electrode to the other, through the pores in the membrane separating the two electrodes. Depending on the number and size of the pores, the buffer composition, and the applied voltage, the current can be pA-mA in magnitude and is easily detected with a simple electronic circuit. Unbound NA electrophoretically flowing through the pores will affect the measured current very slightly and briefly. However, a bead blocking a pore will steadily block a significant fraction of the current flowing through that pore, which is easily detected. Additional pores blocked by additional beads will cause additional blockades in current. This blockage in current is an easily and distinctly measured "YES" signal.

If the sample does not contain NA complementary to that present on the bead, a "negative" signal should be returned since there is no block of current. As mentioned above, unbound NA will not significantly affect the current magnitude through the pores. However, even the beads without any bound target NA may have some negative charge on them due to the capture probe itself and/or other surface ligands and could be electrophoretically driven to the pore.

According to various embodiments of the invention, we have three solutions to this possibility: 1) The capture probe complementary sequence on the beads will not consist of NA, but of peptide nucleic acids (PNA), neutral molecules with the demonstrated ability to hybridize to specific complementary NA sequences. Therefore, PNA-conjugated beads to which no NA has hybridized would not respond to an electric field. 2) Establishment of a fluid flow from the bead-free compartment to the bead containing compartment. For a range of flow rates and applied voltages (which change the rate of electrophoresis), the net flow of the beads with no bound target NA would be away from the pore, leaving them open and conductive. This fluid flow could be established osmotically, electroosmotically (through a fixed negative surface charge of the membrane and pore) or hydrostatically, for example. When the target NA is bound to the beads, the amount of negative charge on the beads increases the electrophoretic mobility sufficiently to overcome this flow and result in its motion toward the pore and ultimate blockage of it. 3) Capping of negatively charged carboxyl groups on the bead surface with ethanolamine or similar reagent to render them neutral. Alternatively, unreacted amine groups on a bead surface could be capped using an appropriate carboxylic acid. Through a combination of solutions 1), 2), or 3), we expect that the measured current through the pores to remain high when the NA sample does not contain any complementary target NA, resulting in an easily read "NO" signal.

In one embodiment, commercial track-etched membranes with a precise pore size (e.g., approximately 10 nm to approximately 5 μm nm diameter) are sandwiched between two plastic chambers with openings facing the membrane. The membranes preferably should be hydrophilic to enable the wetting and filling by an aqueous electrolyte. The chambers are filled with an electrolyte solution (e.g., 0.1-1 M NaCl in buffered water, other strong electrolyte). Neutral or negatively charged plastic beads (e.g., unmodified or functionalized polystyrene) of a diameter equal to or greater than the membrane pore size are chemically functionalized (e.g., commerically available polystyrene beads presenting carboxyl group are reacted with a crosslinker such as 1-ethyl-3-(3-dimethylaminopropyl) carbodiimide (EDC) to facilitate their conjugation to amine groups). Reaction of these beads with PNA capture probes constructed with a sequence complementary to that of the NA desired to be detected and also having a terminal amine will covalently attach the NA to the beads. Alternatively, beads with surface amine groups could be used with PNA capture probes possessing a terminal carboxyl group to construct the bead-PNA conjugates. These beads are added to one chamber but not the other.

The NA solution to be measured is processed to yield single-stranded NA; this solution is mixed with the beads in the chamber (or separately and then added to the chamber) on one side of the pore. Electrodes (for example Pt or Ag/AgCl), one in the chamber on each side of the pore, apply an electrical potential difference between the two chambers, of a polarity to force the negatively charged species to flow to the pore. The current flowing through the pore is measured using a commercial current meter or a current-to-voltage converter constructed from commercial electronic components. The current is monitored for step-like decreases as the beads with bound target NA are driven to the pores and held there by the electric field, blocking the current. Measurement of the blocked current indicates the presence of the target NA, and a simple electrical circuit or computer program can signal its presence.

An alternative embodiment comprises a micropipette tapered to approximately a 2 μm diameter pore and approximately a 3 μm diameter polystyrene beads to which uncharged peptide nucleic acid (PNA) probe molecules have been conjugated. As the target NAs hybridize to the complementary PNA-beads, the beads acquire negative charge and become electrophoretically mobile. An applied electric field guides these NA-PNA-beads toward the pipette tip, which they obstruct, leading to an indefinite, electrically detectable, partial blockade of the pore. In the presence of non-complementary NA, even to the level of single base mismatch, permanent pore blockade is not seen. Application of this platform to detection of the anthrax lethal factor sequence has been shown.

Example 1

1. Materials

All chemicals were purchased from Sigma-Aldrich (St. Louis, Mo.) unless otherwise noted. Amine and carboxylic acid-functionalized 3 μm diameter polystyrene microspheres (beads) were purchased from Polysciences, Inc. (Warrington, Pa.). All oligonucleotides (PNA and single stranded DNA) were purchased from Bio-Synthesis, Inc. (Lewisville, Tex.) as HPLC purified and lyophilized powders. Single stranded DNA (ssDNA) molecules used were: (a) polyT (5'-TT TT TT TT TT TT TT TT TT TT-3'), (b) polyA (5'-AA AA AA AA AA AA AA AA AA AA-3'), (b) anthrax LF (5'-GG AT TA TT GT TA AA AA AA AA-3'), and (c) anthrax LF with single base mismatch (5'-GG AT T$\underline{C}$ TT GT TA AA AAAA AA-3'). The PNA capture probes used were (a) Amine-TT TT TT TT TT TT and (b) Amine-$(CH_2CH_2O)_{12}$-CC TA AT AA CA AT. Pre-pulled borosilicate micropipettes with 2 μm pore diameter were purchased from World Precision Instruments, Inc. (Sarasota, Fla.).

2. Probe Coupling to Microspheres (Beads)

Fifty μL of 3 μm, carboxylic acid-functionalized polystyrene microspheres at $1.69 \times 10^9$/mL were washed three times with MES Buffer (60 mM 2-(N-morpholino) ethanesulfonic acid, pH 5.5). After each wash the microspheres were centrifuged at 14,000 rpm for 15 minutes; at the end of the last wash they were resuspended into 0.6 mL Coupling buffer (100 mM 1-[3-(dimethylamine) propyl]-3-ethylcarbodiimide (EDC) in MES Buffer). Ten nmol of amine-functionalized PNA probes were added to the coupling buffer and incubated at 50° C. for 3 hours. The beads were then washed once in 0.4×SSC buffer (60 mM NaCl, 6 mM trisodium citrate, 0.1% Triton X-100, pH 8), resuspended into 0.6 mL of coupling buffer containing 100 mM ethanolamine, and incubated at 50° C. for one hour to cap any remaining unreacted carboxylic groups with ethanolamine. After the last coupling step, the beads were washed 4 times in 0.4×SSC buffer and were stored in PBS buffer at 4° C.

3. Hybridization Assay

Prior to DNA incubation, PNA-beads were washed twice in 0.4×SSC buffer and once in hybridization buffer (750 mM NaCl, 10 mM Tris-HCl, pH 7.0), and were resuspended in 100 μL of hybridization buffer. The PNA-beads were divided between two separate 1.5 mL centrifuge tubes. To one tube 1 nmol of 20-mer target DNA with sequence complementary to the PNA on the beads was added, and to the other (control) 1 nmol of 20-mer non-complementary DNA was added. The tubes were placed on a mechanical rotator and incubated overnight at room temperature. After incubation, the beads were washed with 0.4×SSC buffer 3 times.

4. Zeta Potential, Electrophoretic Mobility, and Size Measurements

Following resuspension of the beads in 1 mM KCl, pH 7.0 at 25° C., a Zetasizer Nano-ZS (Malvern Instruments) was used to characterize bead zeta potential and electrophoretic mobility as well as their size using dynamic light scattering. The mean and mode diameters measured for the carboxylic acid beads were 3680 nm and 3580 nm, respectively, and the mean and mode diameters of the amine beads were 3250 nm and 3090 nm, respectively. The zeta potential and electrophoretic results are shown in Table 1, Table 2, and Table 3.

5. Sensor Apparatus and Electrical Measurements

FIG. 2A is a diagram that illustrates an embodiment in which an oligonucleotide detection system 30 uses a tapered micropipette to provide a pore through the membrane separating the chambers. In the embodiment shown, the detection system 30 comprises a first chamber 32 and second chamber 34 for containing a fluid 36. The first 32 and second 34 chambers are separated by a membrane 38 through which the pore extends. The pore in this embodiment is provided by a micropipette 40 that has a tapered tip 42. In this regard, the diameter of the inner lumen of the pipette decreases from the untapered end 54 toward the tapered tip 42 as illustrated in FIG. 2B and FIG. 2C. A negative electrode 44 is positioned in the first chamber 32 and a positive electrode 46 is positioned in the second chamber 34. The two electrodes 44, 46 are connected to a direct current (DC) voltage source 48 that provides the electric potential and a device for measuring current 50. The pipette 40 runs through the membrane 38 with the lumen in the pipette forming a fluidic channel 52 through the membrane and between the chambers. Beads to which uncharged peptide nucleic acid (PNA) probe molecules have been conjugated are added to the first chamber 32 at the first end 54 of the pipette 40. FIG. 2B is a detailed diagram of the pipette tip portion. The negative charge 58 and positive charge 60 within the fluid are shown in the figure. When the PNA-beads come into contact with specific target NA, the NA binds to the PNA and the bead-molecules 56 become negatively charged and move through the channel 52 and toward the opening in the tip of the pipette. Referring also to FIG. 2C, the beads 56 are sized to be larger than the opening in the pipette tip and, as a result, are trapped in the pipette tip. This causes a change in measured electrical current. FIG. 2D is a graph showing the current measured over time before bead blockade. FIG. 2E is a graph showing the current measured over time after bead blockade. Together, FIG. 2D and FIG. 2E show the step-function decrease in current before and after bead blockade.

In one embodiment of the invention, two identical chambers made of polydimethylsiloxane (PDMS) connected by a 1 mm diameter opening were sealed to a glass microscope slide following activation with oxygen plasma. A pre-pulled borosilicate micropipette with outer diameter of 1 mm and nominal inner tip (pore) diameter of 2 μm was placed in the opening between the two chambers and sealed with vacuum grease so that the micropipette is the only connection between the two chambers. The platform was mounted on an inverted optical microscope (Leica DMIRB).

The chambers were filled with identical volumes of buffer (1 mM KCl, 10 mM HEPES, pH 7.0); Pt electrodes were placed in each chamber, away from the pipette entrances. A potential difference of 25 V was applied between the electrodes, and the resultant current was amplified by a transimpedance amplifier and logged using acquisition hardware at 1 kHz (PCI 6052E, National Instruments) and LABView software (National Instruments). After initial set up and baseline current recording, 10 μL of the bead suspension (in 1 mM buffered KCl) were injected into the micropipette and were observed optically while the system was monitored electrically. In the absence of applied voltage, motion of the beads within the capillaries was not observed. The voltage was not found to be critical and could range from lower values to higher values provided that the voltage is not so high as to create an arc or break the conjugation.

6. Results and Discussion

Initial experiments relied on pH to modulate the charge of carboxylic acid- or amine-terminated polystyrene beads thereby manipulating their electrophoretic mobility and ability to effect pore blockage. FIG. 3A is a graph of the measured current over time and shows the ionic current drop caused by pore blockade from an embodiment of the invention where carboxylic acid-functionalized beads were used at pH 7.0. The blockade was reversible, as seen from the increase in current measured following reversal of the applied voltage (dashed line). FIG. 3B is a graph of the measured current over time and shows the ionic current drop caused by pore blockade from an amine-functionalized bead at pH 7.0, according to another embodiment of the invention. The blockade also was reversible, as seen from the increase in current measured following reversal of the applied voltage (dashed line).

At pH 7.0, the carboxylic acid beads carried substantial negative surface charge (zeta potential=−87 mV) due to the deprotonation of carboxylic acid groups ($pK_a$~4.5) thereby making the beads responsive to an electric field. With the capillary tip at high electric potential (positively charged electrode at tip), we observed the beads to move inside the capillary toward the pore ("sensing zone") and block it stably and indefinitely. Reversal of the applied potential caused the bead to move in the opposite direction, re-opening the pore and returning the magnitude of the measured current to the initial value. This behavior was consistent and repeatably measurable, with some variation in the magnitudes of open capillary current and blocked current observed with different capillaries. The bead blockade in one of the capillaries could not be reversed after the third blockade, but the other three capillaries were repeatably reversible and measured as long as desired. When the same experiments were conducted at pH 2.5 (below the carboxylic acid bead $pK_a$, measured zeta potential=−1.79 mV) the beads were observed to be immobile and no pore blockade could be achieved. Bead blockades were observed for applied potentials between 5V and 25V; all measurements described below were conducted with an applied potential of 25V.

Example 2

Similar experiments were conducted with amine-terminated beads that are positively charged at pH 7.0 ($pK_a$~9.5, zeta potential=+69 mV at pH 7.0). When a potential of sign opposite to that used in the carboxylic acid bead experiments above was applied, the amine beads were observed to move toward the pore and block it, also producing stable, indefinite, and reversible reduction in the measured current (FIG. 3B). When repeated at pH 11.5, above the bead $pK_a$, the deprotonated and neutral amine beads (zeta potential=+6.3 mV) still moved in the same direction, but more slowly and with insufficient driving force to block the pore. This most likely resulted from electroosmotic flow caused by the deprotonated silanol (Si—OH) groups ($pK_a$~4) on the capillary surface. To confirm this, we microscopically examined the same beads and solution above the planar surface of a borosilicate glass petri dish, and observed that the beads moved only when close to the glass surface, where the electro-osmotic flow is largest. This is also consistent with the complete immobility of the carboxylic acid beads at acidic pH, since both the silanol groups on the capillary surface and the carboxylic acid groups on the beads are protonated and neutral. We presume that, in the experiments with the carboxylic acid beads at neutral pH, the force on the beads due to the electric field acting on the charged beads is greater than the opposing force due to electro-osmotic flow, thereby enabling the beads to be driven to the pore.

FIG. 3A and FIG. 3B show a larger fraction of blocked current obtained with the amine beads compared to the carboxylic beads (81% vs. 24%). In general, from measurements of the carboxylic acid beads in four capillaries and amine beads in three capillaries, use of the amine beads generally resulted in higher blockages (48%-91%) than the carboxylic acid beads (4.7%-66%). Optical observations indicated that the amine beads were typically immobilized closer to the capillary tip than the carboxylic acid beads and it was common to observe some of the amine beads passing completely through the capillary tip. Since the amine beads were on average smaller than the carboxylic acid beads, this and additional observations suggest that the magnitude of the blockade is highly dependent on the relative sizes of the beads and the capillary tip.

Example 3

In further support of this, a subsequent experiment with the carboxylic acid beads in a different capillary (with the same nominal pore diameter of 2 µm) resulted in microscopic observation of some of the beads passing through the pore and, for those that blocked the pore, a larger reduction of current (63% average current blockage). Since the carboxylic acid beads in this experiment were drawn from the same batch as the carboxylic acid beads in previous experiments, complete passage of the beads through the pore suggests that the tip diameter of the micropipette was larger than the ones used in previous experiments. Additionally, measurement of the carboxylic acid beads in another capillary showed a reproducible bimodal blockade current (average blockade percentage of 24% and 6.9%) and two reproducible immobilization locations (with the 24% block occurring closer to the capillary tip) as the voltage was reversed and the experiment repeated. Since this measurement was obtained with one capillary, this suggests that beads of two different sizes or shapes were separately participating in the blockade.

The current measured for carboxylic acid beads passing completely through the tip of one capillary displayed similar characteristics to previous reported measurements of beads traversing conical capillaries, specifically with respect to the rapid decrease in blockade current as the bead passes through the tip to the external solution. However, we do see a difference from this previous work in that the passage time of the bead through the tip is approximately 40 ms, significantly longer than the 1 ms times previously reported for 2 µm diameter colloids. This is most likely due to the transport of the carboxylic acid beads being slowed by the opposing electro-osmotic flow. This is also supported by experiments with the amine beads, which were observed microscopically to pass through the capillary tip but no blockade currents were able to be resolved with 1 kHz data acquisition. The magnitude of the reduction in current measured during the passage of the carboxylic acid beads (12%, an increase in resistance of 5.65 MΩ) was consistent with previous work reported with similar systems.

Example 4

We also developed a simple analytic model calculating the increase in resistance caused by the presence of a spherical particle in a conical channel with circular cross-section based on Gregg and Steidley's model of resistive pulse from particles in a cylindrical channel.

The model predicts increasing blockade resistance with increasing ratio of particle radius to capillary radius $$\frac{r_p}{r_c}.$$

For a spherical particle fully contacting the interior of a conical capillary with circular cross-section, $$\frac{r_p}{r_c}$$

is close to unity and the model predicts complete block of the current. None of our measurements showed complete blockades, although one capillary measured with the amine beads showed 90% average block. These measurements of incomplete block indicate that the particles did not fully contact the capillary interior, possibly due to non-circular cross-sections of the particle or capillary, presence of asperities on the bead or capillary surfaces, or adherence of the particle to the capillary wall before full contact. Evidence from the previously discussed carboxylic acid beads with a particular capillary supports variation in bead size or shape in that the bimodal distribution of blocked currents was quite repeatable and correlated with microscopic observations.

Although the model assumes circular particle and conical capillary cross-section, its parameterization in $$\frac{r_p}{r_c}$$

can be seen alternatively in terms of the particle and capillary cross-sections as $$\frac{r_p}{r_c} = \frac{\sqrt{Area_{particle}}}{\sqrt{Area_{capillary}}} \text{ or } \frac{r_p}{r_c} = \sqrt{1 - \frac{Area_{gap}}{Area_{capillary}}}$$

and therefore as $$\frac{r_p}{r_c}$$

increases, $$\frac{Area_{gap}}{Area_{capillary}}$$

decreases. In this way, we may understand that spherical particles blocking a conical capillary with elliptical cross-section would create larger blockades for smaller particles (thus also blocking closer to the capillary tip) because the cross-sectional area of the gap would decrease, roughly translating to an increased $$\frac{r_p}{r_c}$$

in our model. Therefore in our model, the size of the resistance increase depends on eccentricity of the particle or capillary cross-sections and the particle size. For beads plugging pores, we experimentally observed resistance increases in the range of 38-430 MΩ for amine beads (48%-91% block) and 2-78 MΩ for carboxylic acid beads (4.7%-66% block). For the smaller 3150 nm diameter amine beads, the model yields resistance increases of 38-430 MΩ for $$\frac{r_p}{r_c}$$

of 0.87 to 0.985. For 3600 nm diameter carboxylic acid beads the model yields ΔR of 2-78 MΩ for $$\frac{r_p}{r_c}$$

of 0.54 to 0.93.

We modeled the bead electrophoretic force by equating it to the drag force on the bead when it is moving with constant speed. The measured mobility is the proportionality constant between the speed and the electric field. By modeling the capillary as a simple cone, we estimated the electric field in the capillary as a function of position and found forces between 1.36 and 5.44 nN as the capillary radius tapered from two bead radii to one bead radius.

Example 5

Next, nucleic acid detection was measured using 20-mer polyA ssDNA as a simple target sequence and PNA-beads conjugated with 12-mer polyT PNA as the complementary probe. To assess the PNA conjugation to the carboxylic acid beads, the beads' zeta potential before PNA conjugation was measured to be −87 mV, after ethanolamine capping +5.75 mV, and after three washes with 0.4% SSC buffer −4.39 mV. After capping and washing, the beads were observed to aggregate. Without incubation DNA, the PNA-beads in the micropipette were seen to follow the electro-osmotic flow away from the pipette tip, indicating that the PNA-beads alone were unable to block the pore. Incubation of the PNA-beads with polyA target ssDNA resulted in well-dispersed beads with a measured zeta potential of −71.1 mV, and motion toward the pipette tip in the same applied voltage, ultimately blocking it (FIG. 4B). These current blockades were stable, indefinite, and reversible.

Example 6

In a control experiment, the same polyT PNA-beads as above were incubated with non-complementary 20-mer polyT ssDNA, resulting in a bead preparation with a measured zeta potential of −46.7 mV, which indicated a significant amount of non-specific binding of DNA to the beads. Microscopic observation of the control beads showed movement of the beads to the pore, which they temporarily blocked and then moved back down the pipette away from the pore along with the electro-osmotic flow. Simultaneous electrical measurement showed a transient current blockade of up to approximately 10 seconds long (FIG. 4F). This transient blockade was observed infrequently, with most of the control beads unable to block the pore.

Figure 4C:
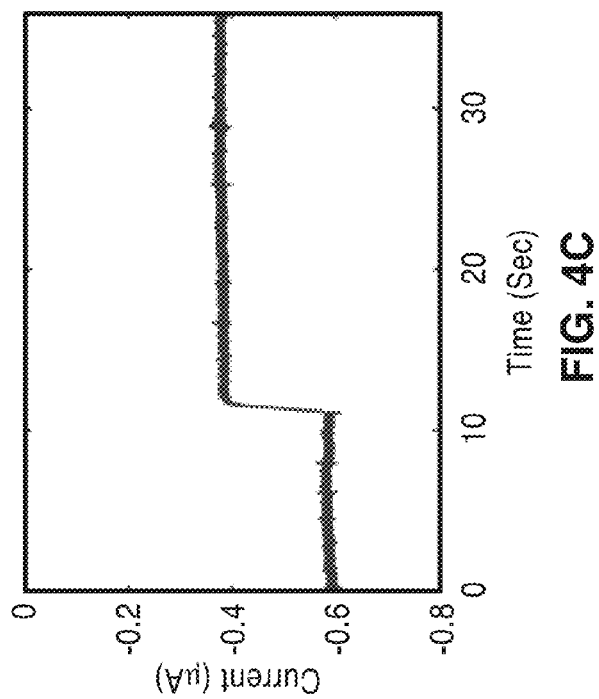
FIG. 4C is a graph corresponding to FIG. 4A and FIG. 4B showing the resultant measured current, according to an embodiment of the invention.
Figure 4A:
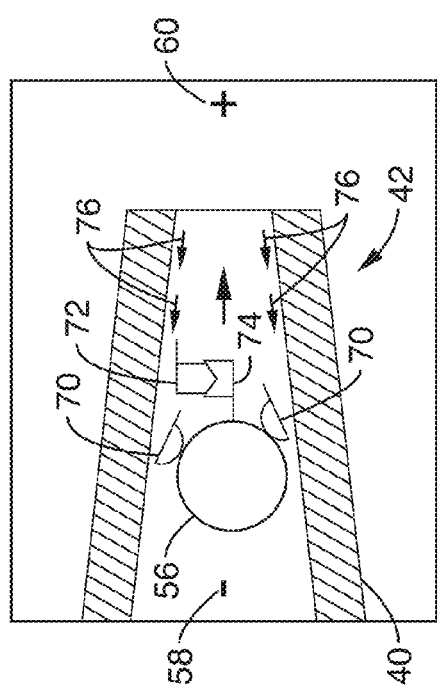
FIG. 4A and FIG. 4B are schematic diagrams of the motion of a PNA-bead hybridized to target NA under an applied potential, according to an embodiment of the invention.
Figure 4B:
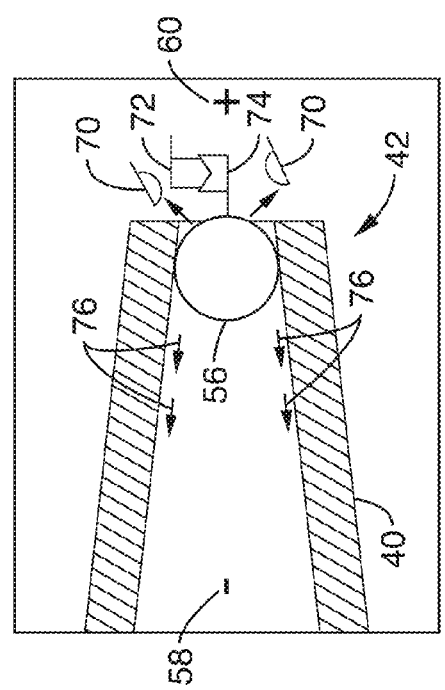
Figure 4F:
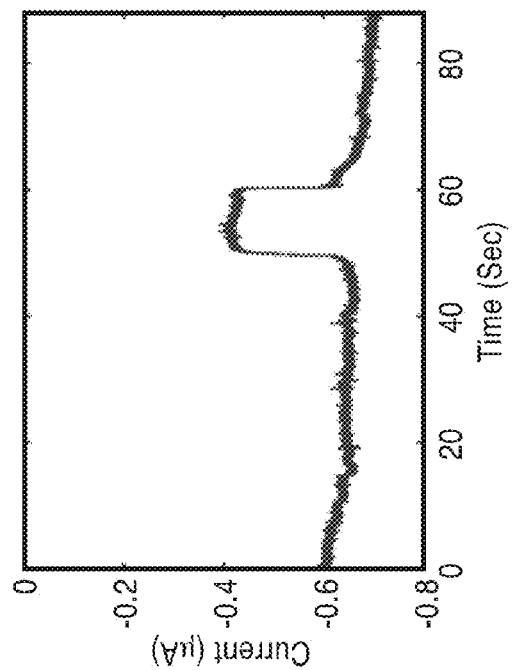
FIG. 4F is a graph corresponding to FIG. 4D and FIG. 4E showing the resultant measured current, according to an embodiment of the invention.
Figure 4D:
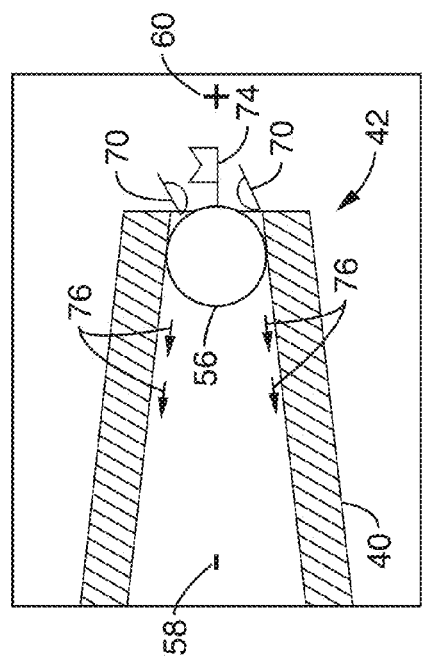
FIG. 4D and FIG. 4E are schematic diagrams of the motion of a PNA-bead without hybridization to target NA under an applied potential, according to an embodiment of the invention.
Figure 4E:
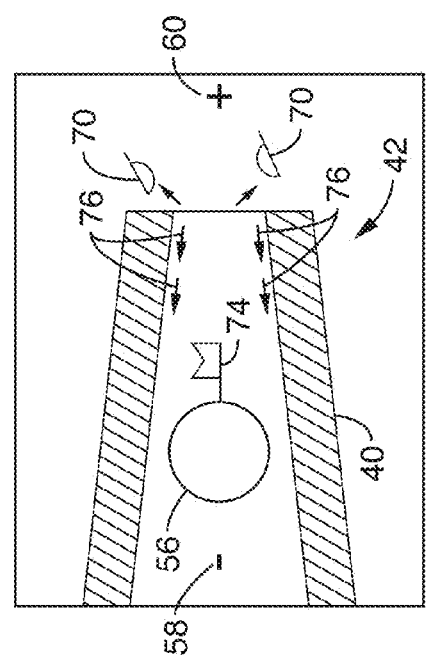

FIG. 4A through FIG. 4F schematically illustrate our observed motion of a PNA-bead with and without hybridized target NA under an applied potential, according to an embodiment of the invention. These figures give detailed views of what is shown in FIG. 2B and FIG. 2C. FIG. 4C and FIG. 4F are graphs of the corresponding resultant measured current. Referring to FIG. 4A, when a PNA-bead 56 with non-specifically bound ssDNA 70 and specifically bound ssDNA 72 hybridizes to PNA 74 on the bead 56, the bead becomes negatively charged and electrophoretically mobile even in the presence of opposing forces 76. Examples of these opposing forces comprise hydrostatic force, osmotic force and electro-osmotic force. FIG. 4B is a diagram illustrating that in the strong electric field at the pipette tip 42 induced by the applied electric potential, the non-specifically bound DNA 70 is removed from the bead 56, but the hybridized DNA 72 is not, leaving the bead with sufficient negative charge to remain blocking the pore indefinitely. FIG. 4C is a graph of the measured current over time and shows the measured permanent current blockade for PNA-beads incubated with complementary polyA DNA, corresponding to FIG. 4A and FIG. 4B. FIG. 4D and FIG. 4E illustrate that for PNA-beads 56 incubated with only non-complementary DNA 70, any DNA bound to the bead is non-specific; the strong electric field at the pipette tip 42 removes the non-specifically bound DNA 70, reducing the bead's charge sufficiently so that the opposing force 76 is able to remove the bead 56 from the pipette tip 42. FIG. 4F is a graph of the measured current over time and shows the transient current blockade measured for PNA-beads incubated with non-complementary polyT DNA, corresponding to FIG. 4D and FIG. 4E.

The control and target experiments were repeated at least three times; measured zeta potentials and electrophoretic mobilities are listed in Table 1 with the qualitative results of the electrical measurements. Quantitatively, the magnitude of the blockades measured for the target DNA was consistent between the three capillaries (average blockades: 22.0%, 25.6%, and 25.6%). The blockade of one of the capillaries could not be reversed after five measurements.

Table 1 provides a summary of experimental results for target and control samples: Zeta potential and electrophoretic mobility measured after ssDNA incubation and results of micropipette electrical measurements.

We conclude that incubation of the beads with ssDNA results in non-specific binding for both complementary and non-complementary sequences. In the control experiments, the DNA binding to the bead is entirely non-specific, however, less strongly bound than the complementary DNA. Still, the non-specific DNA beads are negatively charged and electrophoretically mobile, allowing them to be driven to the pore. In the pore, the electric field generated by the voltage source is sufficiently strong to remove the non-specifically bound DNA from the bead, which causes a reduction in bead charge and electrophoretic mobility, enabling the electro-osmotic flow to exceed the electrophoretic force and carry the bead away from the pore.

Example 7

To estimate these forces, we used the model described above to analyze the electric field near a trapped bead and determine the electric force on a 20-mer ssDNA on the bead surface. Based on the average currents measured for PolyA ssDNA-PolyT PNA beads in three capillaries, a force of 13.9 pN is obtained from the model for the 20-mer ssDNA on the bead surface. This force is less than the 57 pN rupture forces measured for 8 bp DNA-PNA with optical tweezers.

Example 8

To further investigate the selectivity of the sensor, we detected ssDNA with a non-repeating sequence, a 12-mer portion of a gene encoding the anthrax lethal factor. To allow direct comparison with the previous experiment detecting 20-mer ssDNA, we added an 8-mer polyA tail to the 12-mer anthrax sequence. To enhance the binding of complementary ssDNA and minimize non-specific binding, a PEG spacer was added to the amine-functionalized 12-mer complementary PNA capture probe. After PNA conjugation, capping with ethanolamine, and washing, the measured zeta potential of this PNA-bead preparation was −2.75 mV. The PNA-beads were divided into two volumes, one incubated with 20-mer target anthrax ssDNA and the other with control 20-mer polyT ssDNA. Measured zeta potentials after incubation were −56.7 mV for target beads and −39.0 mV for control beads. As with the previous experiments described above, the presence of complementary DNA led to permanent blockades, whereas its absence led to transient or no blockade. The results are illustrated in FIGS. 5A and 5B. Specifically, FIG. 5A is a graph of measured current over time showing the permanent ionic current drop caused by beads incubated with target anthrax ssDNA. The blockade was reversible and repeatable, as seen by reversals of the applied voltage (dashed lines). FIG. 5B is a graph of measured current over time where transient ionic current drops were seen occasionally with beads incubated with the non-complementary, control ssDNA.

Even in experiments with the control DNA in which transient blockades were measured, only a few beads were seen to transiently block the current, with the majority of the beads being inadequately mobile in the electric field to block the pore. These experiments were repeated three times and the results are summarized in Table 2.

Table 2 provides a summary of experimental results for target and control samples: zeta potential and electrophoretic mobility measurements after each hybridization experiment and results of electrical measurements.

Example 9

The capillary blockade and its magnitude were highly repeatable. In six capillaries tried (three listed in Table 2 and three discussed below and listed in Table 3), blockades were observed for all six (average blockade: 21.5%, 23.0%, 24.6%, 21.8%, 23.9%, and 21.1%). In each of the capillaries measured, following blockade, the voltage was reversed to remove the bead from the capillary tip to attempt further blockades. In one of the six capillaries, after five detection events, the bead was not able to be removed from the blockade site with reversal of applied voltage and the experiment was terminated.

Example 10

To investigate the sequence specificity of the sensor, we created a 20-mer ssDNA with the same sequence as the 20-mer ssDNA for the anthrax LF experiment described above but with a single base mismatch. The measured zeta potential after PNA conjugation, capping with ethanolamine, and washing was −7.39 mV. As described above, the PNA-beads were divided into two volumes, one incubated with the anthrax LF ssDNA and one with the single base mismatch ssDNA. Table 3 summarizes the results of three separate experiments, which are consistent with our previous results described above. Occasional transient blockades were observed in the presence of the mismatch DNA sample; permanent blockades were recorded only in the presence of target anthrax ssDNA.

Table 3 provides a summary of experimental results for target and single base mismatch control samples: zeta potential and electrophoretic mobility measurements after each hybridization experiment and results of electrical measurements.

Comparison of beads incubated with complementary target ssDNA in Table 1 (target: poly A) and Tables 2 and 3 (target: Anthrax-LF) show that the magnitudes of the zeta potentials and mobilities in Table 1 were larger than those in Tables 2 and 3. A possible explanation for these results is the lack of registration required for the hybridization of polyA ssDNA, compared to the exact registration required for hybridization of Anthrax ssDNA. Longer ssDNA targets may improve the electrophoretic mobility of the hybridized beads, while longer strands of non-specifically bound ssDNA would still be expected to detach from the bead in the strong electric field at the sensing zone to result in only transient ionic current blockades.

Example 11

The limits of detection were probed by serially diluting the 20-mer target anthrax ssDNA in hybridization buffer and repeating the incubation with PNA beads and nanopore measurement as described above. Pore blockade was observed down to a concentration of 10 pM. At this concentration, we observed some beads only transiently blocking the pore before permanent block was achieved, indicating the presence of both non-specific and complementary ssDNA bound to the beads, as well as a smaller amount of bound complementary DNA. We are currently working to reduce this limit through the use of longer target ssDNA oligomers and reducing the scale of the system.

Overall, our system performed as expected for detection of specific DNA sequences. Using the conditions described, polyA or Anthrax were successfully detected in every capillary tried (nine capillaries total), with no false positives (no permanent blockade) observed in any capillary (nine capillaries total), including ssDNA with only a single base mismatch. The lowest DNA concentration successfully detected with our unoptimized system was ~10 pM, an unimpressive detection level compared to other published approaches, including a PNA sandwich-hybridization assay for anthrax with a DNA detection limit of as low as 10 zmol. Yet, this binary detection system could exhibit a very low detection limit if the system were scaled down such that a sub-micron PNA-bead conjugate would assume sufficient charge for electrophoretic mobility and pore blocking upon binding one or a few target DNA molecules. Of course this low detection limit comes at the expense of the capability to determine target DNA concentration.

Nevertheless as discussed above, there are a number of important applications where a binary (yes/no) signal for the presence/absence of the DNA target is sufficient. Further, the large and sustained reduction in current resulting from the blockade of the pore by a PNA-bead conjugate with bound target DNA provides an easily detectable signal for the presence of the DNA target that can be displayed with simple electronics. Using a simple inverting operational amplifier and light emitting diodes, we constructed a binary indicator of the target DNA detection, demonstrating its potential application in a simple, potentially low-cost device.

Example 12

In the next embodiment, work has been done to scale down the system so as to reduce its cost and detection limit. Silicon-based micromachining technology was utilized to create multiple 1 cm² chips comprised of a silicon-supported silicon nitride (SiN) membrane with a single, tapered pore milled through it. A fabrication process was designed that gives fifty-six devices starting with a 4-inch silicon wafer. The first point to consider was the microfabrication of the silicon nitride membrane and nanopore, to ensure that the devices could be made at the desired dimensions.

Figure 6B:
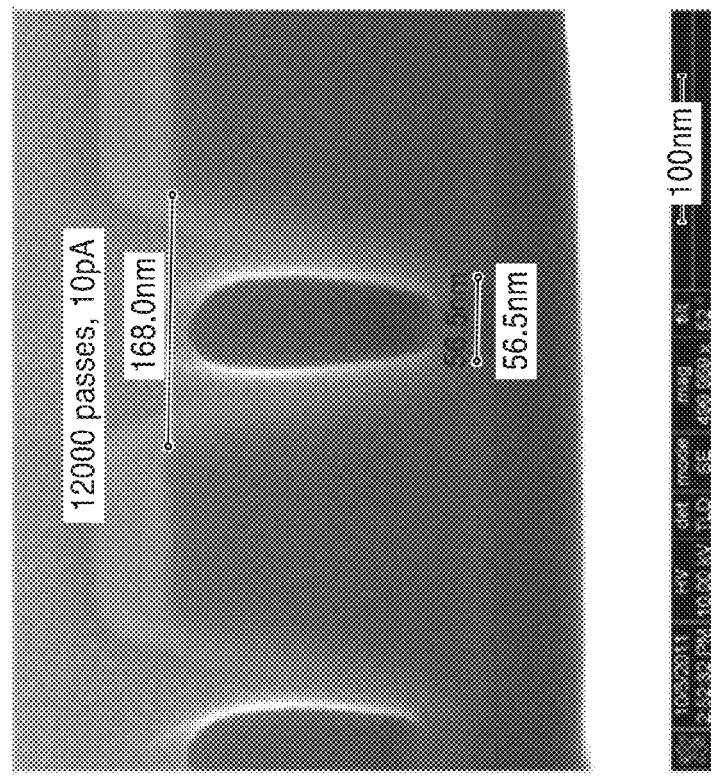
FIG. 6B is a SEM cross sectional image of ~300 nm diameter pores milled into silicon nitride, according to an embodiment of the invention.
Figure 6A:
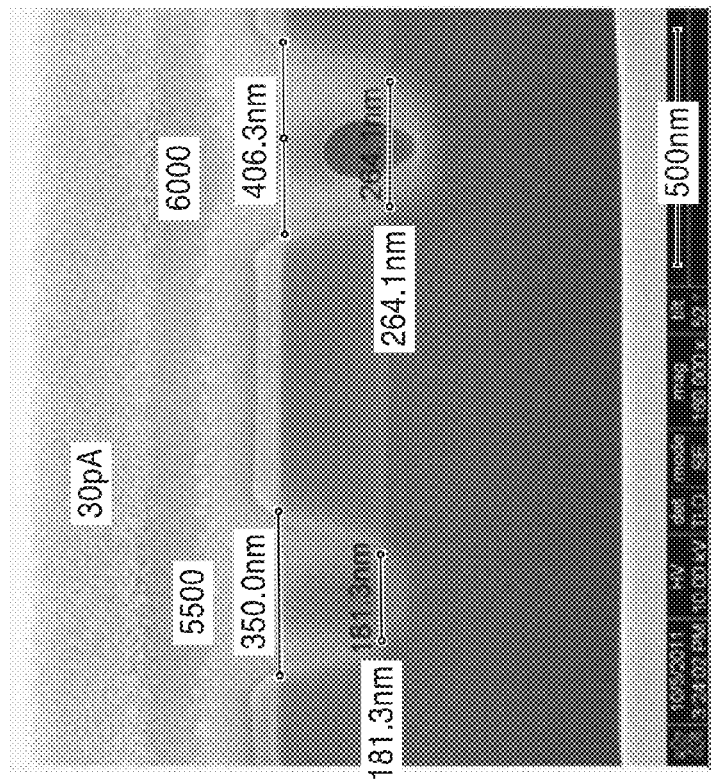
FIG. 6A is a scanning electron microscope (SEM) cross sectional image of ~100 nm diameter pores milled into silicon nitride, according to an embodiment of the invention.

To test the ability of the focused ion beam (FIB) to etch pores down to 100 nm in diameter, FIB parameters such as the number of passes and the ion beam current were varied to determine if 100 nm pores could be milled into a 300 nm thick silicon nitride surface. Initially, the silicon beneath the silicon nitride was left intact (as opposed to etching it away to reveal a freestanding membrane). The resulting pores were filled with platinum and a cross section of the sample was etched to determine the pore dimensions and the depth of etch. FIG. 6A shows a SEM cross sectional view of ~100 nm diameter pores milled into silicon nitride using a focused ion beam (FIB). FIG. 6B shows a SEM cross sectional view of ~300 nm diameter pores milled into silicon nitride using a FIB.

Thus, the parameters for a pore that etched through the silicon nitride were determined visually. The natural tapering of the pore from the FIB works to our advantage, as an opening larger than 100 nm on the bead well side would allow a 100 nm diameter bead to enter the pore. The tapering down of the pore to less than 100 nm ensures that the bead will be securely stuck within the pore with as much contact with the pore as possible. Next, larger sized pores of 300 nm in diameter were etched in silicon nitride to determine the feasibility of changing the diameter of the pores. For the purpose of actual testing with beads, milling 1 µm diameter pores was tested in a freestanding silicon nitride membrane. In this case, the silicon underneath the silicon nitride was already etched away.

Example 13

Figure 7B:
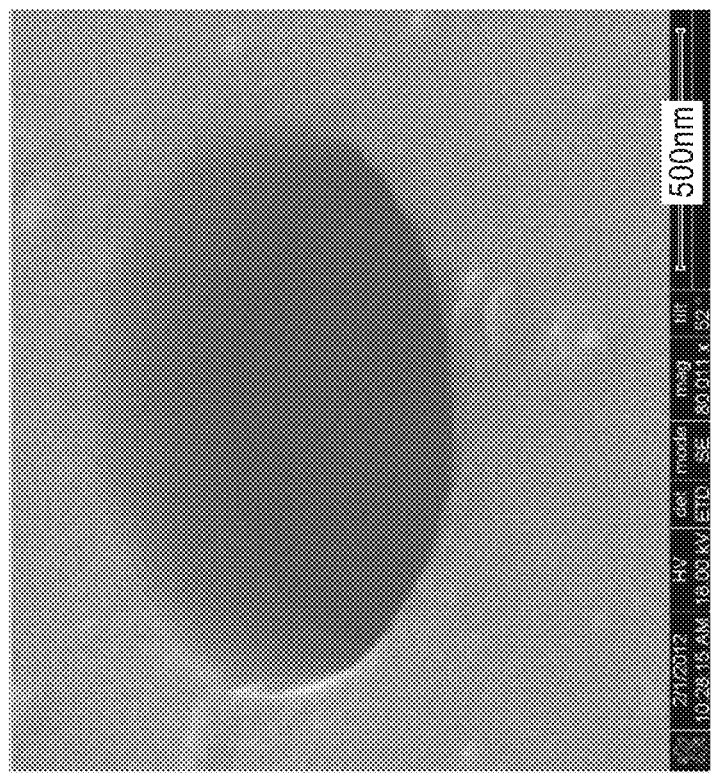
FIG. 7B is also a SEM image of FIB-milled ~1 μm diameter pores, according to an embodiment of the invention.
Figure 7A:
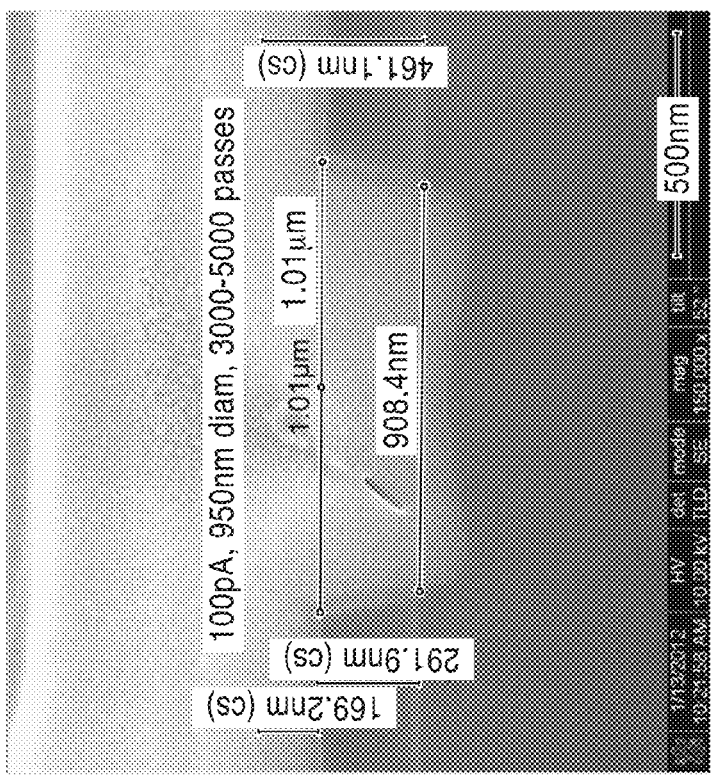
FIG. 7A is a SEM image of FIB-milled ~1 μm diameter pores, according to an embodiment of the invention.

Referring to FIG. 7A and FIG. 7B, a parameter that we found preferable to optimize was the area of the silicon nitride membrane. FIG. 7A and FIG. 7B show SEM images of FIB-milled ~1 µm diameter pores at two different angles. It is preferable to create a membrane large enough to easily mill a pore using the FIB, but still be able to survive the subsequent fabrication steps and general handling after the membrane is created. Initial attempts started at trying to create a membrane that was 0.5 cm in diameter, which led to a membrane survival rate of 0%. From there, we decreased the membrane size until it was determined that a 50 um membrane was small enough to survive the fabrication without breaking.

Example 14

With the successful optimization of the fabrication steps, we have been able to consistently fabricate silicon nitride membrane chips with desired dimensions. For example, we created silicon nitride membranes in the shape of 50 µm×50 µm squares. An embodiment of a fabrication process flow 100 is illustrated in FIG. 8A through FIG. 8G. The fabrication process starts with bare 4-inch silicon wafers 102 as provided by Silicon Valley Microelectronics, Inc., as shown in FIG. 8A. After undergoing a prefurnace clean in piranha and hydrofluoric acid, the wafers are placed in a furnace, where 300 nm thick nitride 104 is grown on both sides of the wafer via low pressure chemical vapor deposition (LPCVD), as shown in FIG. 8B. The frontside etch 106 defines each 1 cm×1 cm device, with the silicon nitride dry-etched using $CHF_3$ gas for 1 minute and 30 seconds, as shown in FIG. 8C. This gas will etch away exposed nitride and will stop etching once silicon is reached. The backside of the wafer is then etched 108 to expose the silicon 102 that will be etched away to create the silicon nitride membrane, as shown in FIG. 8D. The wafer is then placed in an 80° C. bath of 30% KOH for 4 hours to etch away the silicon 102. The nitride 104 acts as a mask to so that only areas with exposed silicon 102 will etch. Once the silicon nitride membrane is made, the wafer is placed into a Sloan evaporator, where 50 nm of chromium 110 is sputtered onto the surface, as shown in FIG. 8E. This conductive layer allows us to view the wafer accurately when using the FIB. Next, the pore 112 is etched with the FIB to our target diameter, as shown in FIG. 8F. Finally, the chromium 110 is etched off and the wafer is diced to create the membranes for this embodiment of the invention, as shown in FIG. 8G.

Example 15

Figure 9A:
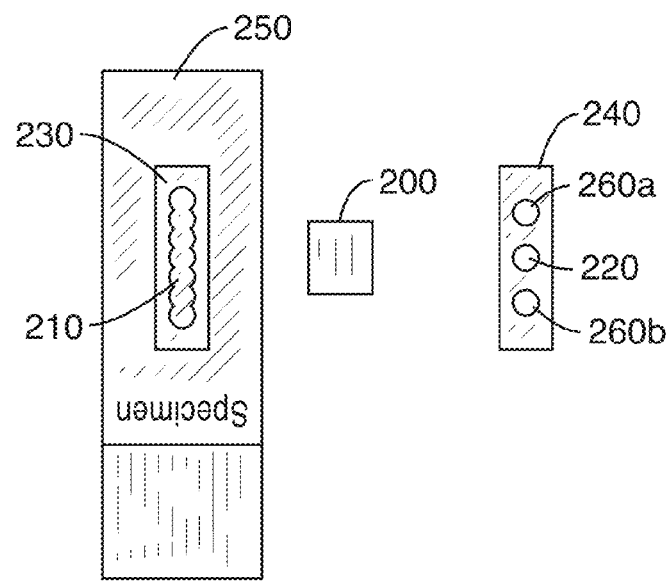
FIG. 9A is an image of a detection system using a chip, fabricated according to FIG. 8A through FIG. 8G, shown unassembled, according to an embodiment of the invention.
Figure 9B:
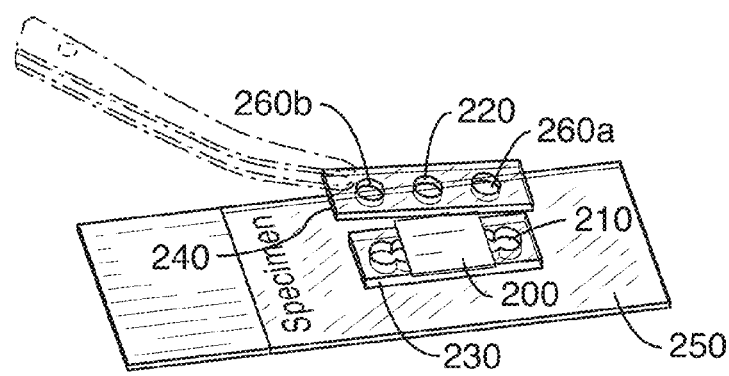
FIG. 9B is an image showing partial assembly of the detection system shown in FIG. 9A.
Figure 9C:
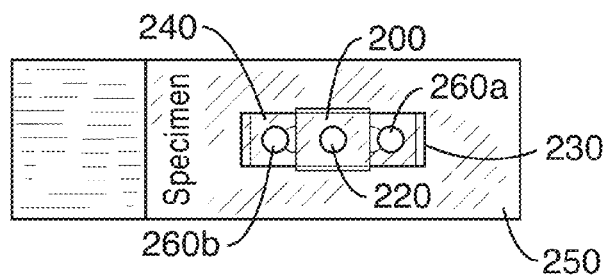
FIG. 9C is an image showing the fully assembled detection system of FIG. 9A and FIG. 9B.

The next area of focus was creating the entire device, with chambers on both sides of the membrane that could easily be filled with buffer and/or bead solution. The best solution was to sandwich the chip in between two small chambers made of polydimethylsiloxane (PDMS) slabs measuring approximately 1 cm×2.5 cm×5 mm thick. To keep fluid from leaking from the chambers, each layer was sealed together with vacuum grease, which made the device airtight. The two electrolyte-filled chambers are fitted with AgCl electrodes to measure ionic current deflections arising from changes in pore conductance. FIG. 9C illustrates an embodiment of the apparatus where a membrane chip 200 containing a <100 nm-diameter pore separates two electrolyte-filled chambers 210, 220. FIG. 9A is an image of the unassembled device comprising, a bottom PDMS slab 230 with a first large chamber 210, a top PDMS slab 240 with a second small chamber 220 and two ports, 260a, 260b a microscope slide 250 and a membrane chip 200 containing a pore. The chambers 210, 220 and ports 260a, 260b are punched into the PDMS slabs 230, 240 using a hole puncher approximately 5 mm in diameter. The bottom PDMS chamber 210 is larger (around 2 cm long) and extends past the chip 200 to allow for this bottom chamber to be filled with buffer solution through one of the top ports. 260a, 260b Referring to the top PDMS slab, 240 the center hole 220 forms the second chamber where the beads and sample will be placed and the two outer holes 260a, 260b provide ports that are fluidly connected to the bottom chamber 210 and allow for the addition of buffer solution into the bottom chamber 210 and the displacement of air. The assembling of the device is illustrated in FIG. 9B. The bottom PDMS slab 230 is attached to the microscope slide 250. Next the membrane chip 200 is layered on top of the bottom PDMS slab 230, followed by the top PDMS slab 240. The layers are sealed airtight so that fluid will not leak out of the chambers. FIG. 9C is an image of the assembled device where the bottom PDMA slab 240 has been sealed to the microscope slide 250, the chip 200 placed on top of the bottom PDMS slab, and the top PDMA slab 240 placed on top of the chip 200. In this figure, the two outer ports 260a, 260b and the second chamber 220 are clearly visible.

A feature is the membrane separating the reservoirs that harbors a single nanopore. Since we are not interested in the stochastic sensing of single independent NA molecules, we can work with larger diameter and longer pores than those described in the literature. All exposed Si or SiN surfaces will be oxidized to present surface —OH groups in water. These —OH groups have the tendency to deprotonate in water giving rise to fixed negative charges on the pore wall. As described above, charging of the pore surface and electro-osmotic motion of fluid through the pore could affect the ability of the bead-PNA with an acquired NA target to form the pore blockade required for NA detection. In order to at least partially neutralize this charge (some electro-osmotic flow may be useful to disrupt blockage by bead conjugates without captured NA and to create mixing), we will conjugate the surface with PEG-silane, a strategy that has been demonstrated in capillary electrophoresis applications for neutralization of glass surface charges in water. PEG is a hydrophilic molecule, ensuring that the pore surface will be wetted by water and will be filled with the analyte solution. To date, we have set up an imaging system on a microscope so that the beads in solution can be seen. With the correct voltage, both carboxylic and amine terminated beads have been seen moving towards the pore.

Example 16

Figure 10:
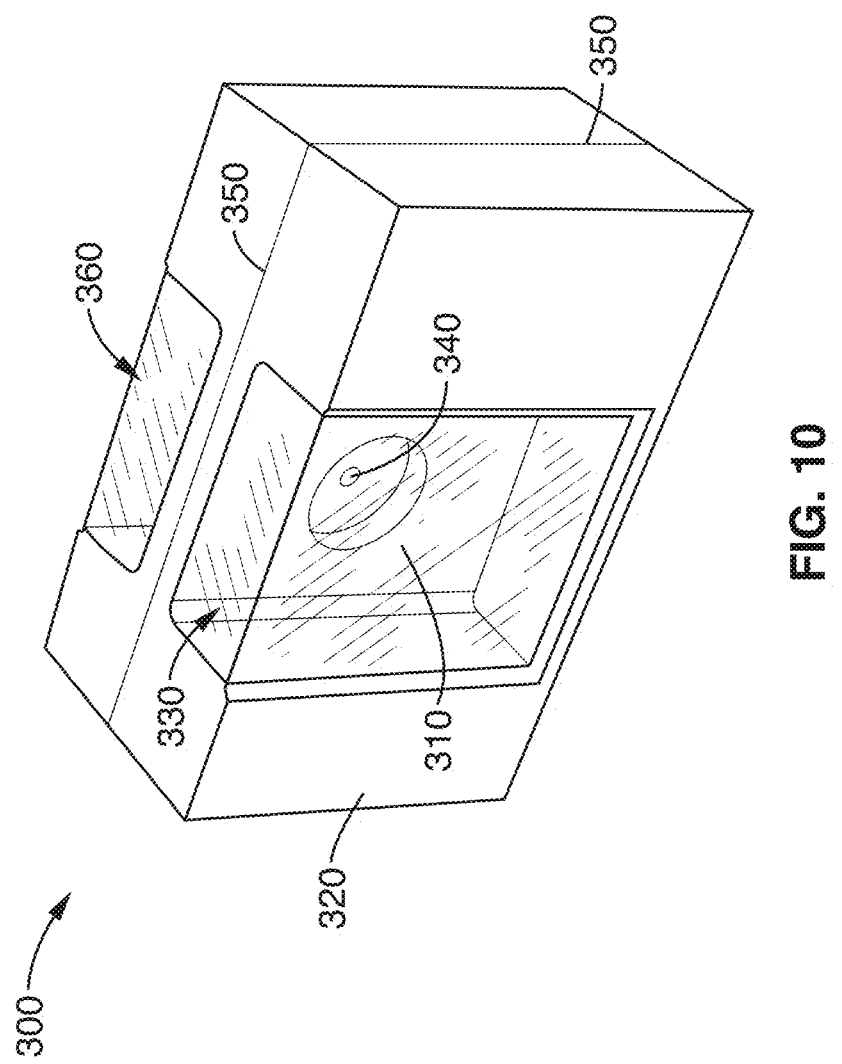
FIG. 10 is a schematic diagram of another embodiment of a apparatus for detecting specific nucleic acid sequences according to the invention.

In an alternative embodiment of the invention, the detection system 300 shown in FIG. 10 involves synthesizing solid-state membranes with pores using a Si on insulator (SOI) wafer processing approach combined with reactive ion etching (RIE) to generate pores through 1-10 μm thick Si membranes. Referring to FIG. 10, the SOI process begins with 500 μM thick Si wafers 310 coated with uniform $SiO_2$ (insulator) layers 320. In one of these, we would micromachine (e.g., by RIE or wet etching) a well 330 through the $SiO_2$ into the Si substrate. Next, the two wafers 310 are bonded 310 $SiO_2$ surface 320 to $SiO_2$ surface 320 through an annealing process. The Si substrate without the well is then thinned to ~1-10 μm in thickness (a variety of choices are available for this step, including simple etching and polishing). RIE will be used to create a pore 340 through the micron-thick layer of Si and underlying $SiO_2$. At more than 1 μm in length, this pore naturally will be at least slightly tapered to a diameter on the far side controlled at <100 nm. Subsequent to pore formation, another Si substrate with the second well 360 previously micromachined into it will be bonded to give the structure illustrated in FIG. 10.

From the foregoing description, it will be appreciated that the invention can be embodied in various ways, which include but are not limited to the following:

1. An apparatus for sequence-specific nucleic acid detection in a sample, the apparatus comprising: a first chamber; a second chamber; a membrane separating said first and second chambers, said membrane having a pore extending through the membrane between the first and second chambers; a first electrode disposed in the first chamber; and a second electrode disposed in the second chamber; wherein when a liquid is introduced into said first and second chambers, wherein when a source of direct electric current is connected to said electrodes with a negative polarity being connected to the first electrode, and wherein when a bead which is conjugated with one or more strands of capture probe nucleic acid that is complementary to a desired target sequence to be detected is subsequently introduced into the liquid in the first chamber, the presence of said target nucleic acid is indicated by a decrease in electric current between the electrodes in relation to electric current between the electrodes prior to introduction of the beads into the first chamber, said decrease in electric current resulting from movement of the bead and the bead causing blockage of the pore.

2. The apparatus of any preceding embodiment: wherein the pore has a length between a first end and a second end; wherein the pore has a diameter that decreases from said first end toward said second end; wherein the bead has a diameter less than the diameter at the first end of the pore; and wherein the pore has a diameter less than the diameter of the bead at a point along the length of the pore.

3. The apparatus of any preceding embodiment, wherein the pore has a diameter ranging from approximately 10 nm to approximately 5 μm.

4. The apparatus of any preceding embodiment, wherein the pore comprises an opening extending through said membrane.

5. The apparatus of any preceding embodiment, wherein the pore comprises a pipette extending through said membrane.

6. The apparatus of any preceding embodiment, wherein the bead comprises unmodified or functionalized polystyrene.

7. The apparatus of any preceding embodiment, wherein the bead has a surface functionalized with amine or carboxyl groups to facilitate cross-linking to a terminal carboxyl or amine group, respectively, added to the terminus of nucleic acid capture probes.

8. The apparatus of any preceding embodiment, wherein the strands of capture probe nucleic acid comprise a peptide nucleic acid.

9. The apparatus of any preceding embodiment, wherein the liquid comprises an electrolyte solution comprising approximately 0.01 M to approximately 1.0 M of an electrolyte in buffered water.

10. The apparatus of any preceding embodiment, wherein said electrolyte is selected from the group comprising of NaCl, KCl, and other strong electrolytes.

11. The apparatus of any preceding embodiment, wherein a single molecule of a desired target sequence can be detected.

12. An apparatus for sequence-specific nucleic acid detection in a sample, the apparatus comprising: a first chamber; a second chamber; a membrane separating said first and second chambers, said membrane having a pore extending through the membrane between the first and second chambers; wherein the pore has a length between a first end and a second end; wherein the pore has a diameter that decreases from said first end toward said second end; wherein the bead has a diameter less than the diameter at the first end of the pore; wherein the pore has a diameter less than the diameter of the beads at a point along the length of the pore; a first electrode disposed in the first chamber; and a second electrode disposed in the second chamber.

13. The apparatus of any preceding embodiment, wherein when a liquid is introduced into said first and second chambers, wherein when a source of direct electric current is connected to said electrodes with a negative polarity being connected to the first electrode, and wherein when a bead which is conjugated with one or more strands of capture probe nucleic acid that is complementary to a desired target sequence to be detected is subsequently introduced into the liquid in the first chamber, the presence of said target nucleic acid is indicated by a decrease in electric current between the electrodes in relation to electric current between the electrodes prior to introduction of the beads into the first chamber, said decrease in electric current resulting from movement of the bead and the bead causing blockage of the pore.

14. The apparatus of any preceding embodiment, wherein the pore has a diameter ranging from approximately 10 nm to approximately 5 µm.

15. The apparatus of any preceding embodiment, wherein the pore comprises an opening extending through said membrane.

16. The apparatus of any preceding embodiment, wherein the pore comprises a pipette extending through said membrane.

17. The apparatus of any preceding embodiment, wherein the bead comprises unmodified or functionalized polystyrene.

18. The apparatus of any preceding embodiment, wherein the bead has a surface functionalized with amine or carboxyl groups to facilitate cross-linking to a terminal carboxyl or amine group, respectively, added to the terminus of nucleic acid capture probes.

19. The apparatus of any preceding embodiment, wherein said strand of capture probe nucleic acid comprises a peptide nucleic acid.

20. The apparatus of any preceding embodiment, wherein the liquid comprises an electrolyte solution comprising approximately 0.01 M to approximately 1.0 M of an electrolyte in buffered water.

21. The apparatus of any preceding embodiment, wherein said electrolyte is selected from the group comprising of NaCl, KCl, and other electrolytes.

22. The apparatus of any preceding embodiment, wherein a single molecule of a desired sequence can be detected.

23. A method for detecting the presence of nucleic acids with a target sequence from a sample, the method comprising: (a) providing a detection apparatus, said detection apparatus comprising: (i) a first chamber; (ii) a second chamber; (iii) a membrane separating said first and second chambers, said membrane having a pore extending through the membrane between the first and second chambers; (iv) a first electrode disposed in the first chamber; and (v) a second electrode disposed in the second chamber; (b) introducing a liquid into said first and second chambers; (c) applying a direct electric current to said first and second electrodes with a negative polarity being connected to the first electrode; (d) measuring electric current between the electrodes as a reference current; (e) introducing, into said first chamber, a bead which is conjugated with one or more strands of capture probe nucleic acid that are complementary to a desired target sequence to be detected; and (f) measuring electric current between the electrodes after introduction of the bead, wherein a decrease in measured electric current indicates the presence of one or more strands of target nucleic acid that are complimentary to the probe sequence conjugated to the bead.

24. The method of any preceding embodiment, wherein said decrease in measured electric current results from movement of the bead and the bead causing blockage of the pore.

25. The method of any preceding embodiment: wherein the pore has a length between a first end and a second end; wherein the pore has a diameter that decreases from said first end toward said second end; wherein the beads have a diameter less than the diameter at the first end of the pore; and wherein the pore has a diameter less than the diameter of the beads at a point along the length of the pore.

26. The method of any preceding embodiment, wherein the pore has a diameter ranging from approximately 10 nm to approximately 5 µm.

27. The method of any preceding embodiment, wherein the pore comprises an opening extending through said membrane.

28. The method of any preceding embodiment, wherein the pore comprises a pipette extending through said membrane.

29. The method of any preceding embodiment, wherein said bead comprises unmodified or functionalized polystyrene.

30. The method of any preceding embodiment, wherein the bead has a surface functionalized with amine or carboxyl groups to facilitate cross-linking to a terminal carboxyl or amine group, respectively, added to the terminus of nucleic acid capture probes.

31. The method of any preceding embodiment, wherein said strands of capture probe nucleic acid comprise peptide nucleic acids.

32. The method of any preceding embodiment, wherein the liquid comprises an electrolyte solution comprising approximately 0.01 M to approximately 1.0 M of an electrolyte in buffered water.

33. The method of any preceding embodiment, wherein said electrolyte is selected from the group comprising of NaCl, KCl, and other strong electrolytes.

34. The method of any preceding embodiment, further comprising hydrostatically, osmotically, or electro-creating a fluid flow through said membrane from the second chamber to the first chamber through a negative surface charge on the membrane and pore.

35. The method of any preceding embodiment, further comprising detecting a single molecule of a desired sequence.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

| Target PolyA | | | Control PolyT | | |
|---|---|---|---|---|---|
| Zeta potential (mV) | Mobility ($10^{-8}$ m$^2$/Vs) | Results | Zeta potential (mV) | Mobility ($10^{-8}$ m$^2$/Vs) | Results |
| −71.1 ± 4.0 | −5.57 | Permanent block | −46.7 ± 4.28 | −3.66 | Transient block |
| −59.3 ± 5.1 | −4.65 | Permanent block | −36.8 ± 4.47 | −2.88 | No block |
| −59.8 ± 4.7 | −4.69 | Permanent block | −32.1 ± 5.3 | −2.52 | No block |

TABLE 2

| Target Anthrax | | | Control PolyT | | |
|---|---|---|---|---|---|
| Zeta potential (mV) | Mobility ($10^{-8}$ m$^2$/Vs) | Results | Zeta potential (mV) | Mobility ($10^{-8}$ m$^2$/Vs) | Results |
| −56.7 ± 6.4 | −4.44 | Permanent block | −39.0 ± 6.50 | −3.06 | Transient block |
| −53.5 ± 5.1 | −4.19 | Permanent block | −30.6 ± 5.78 | −2.40 | No block |
| −50.6 ± 3.7 | −3.96 | Permanent block | −32.8 ± 4.50 | −2.57 | No block |

TABLE 3

| Target Anthrax | | | Anthrax LF Single Base Mismatch | | |
|---|---|---|---|---|---|
| Zeta potential (mV) | Mobility ($10^{-8}$ m$^2$/Vs) | Results | Zeta potential (mV) | Mobility ($10^{-8}$ m$^2$/Vs) | Results |
| −51.1 ± 5.6 | −4.01 | Permanent block | −45.3 ± 4.38 | −3.55 | Transient block |
| −50.3 ± 4.2 | −3.95 | Permanent block | −44.8 ± 3.72 | −3.52 | Transient block |
| −50.9 ± 3.9 | −3.99 | Permanent block | −41.4 ± 5.23 | −3.24 | Transient block |

We claim:

1. A method for detecting the presence of nucleic acids with a target sequence in a sample, the method comprising:
   (a) providing a detection apparatus, said detection apparatus comprising:
      (i) a first chamber;
      (ii) a second chamber;
      (iii) a membrane separating said first and second chambers, said membrane having one or more pores extending through the membrane between the first and second chambers;
      (iv) a first electrode disposed in the first chamber; and
      (v) a second electrode disposed in the second chamber;
   (b) introducing a liquid into said first and second chambers;
   (c) applying a direct electric current to said first and second electrodes with a negative polarity being connected to the first electrode;
   (d) measuring electric current between the electrodes as a reference current;
   (e) preparing at least one bead which is conjugated with one or more strands of capture probe nucleic acid that are complementary to a desired target sequence of a sample to be detected;
   (f) capping charged groups on the prepared beads to render the beads with a neutral charge;
   (g) introducing one or more of the capped beads and a sample into the first chamber to hybridize the capture probe to the desired target sequence; and
   (h) detecting the target sequence by measuring electric current between the electrodes after introduction of the beads and sample and comparing the measured current with the reference current;
   (i) wherein a decrease in measured electric current indicates the presence of one or more strands of target nucleic acid that are complementary to the probe sequence conjugated to the bead; and
   (j) wherein said decrease in measured electric current results from electrophoretic movement of the beads bound to charged target nucleic acid strands to a pore of diameter less than the bead diameter or tapered to a lesser diameter and the beads causing sustained blockage of one or more pores.

2. A method as recited in claim 1:
   wherein each pore has a length between a first end and a second end;
   wherein each pore has a diameter that decreases from said first end toward said second end;
   wherein the beads have a diameter less than the diameter at the first end of the pore; and
   wherein each pore has a diameter less than the diameter of the beads at a point along the length of the pore.

3. A method as recited in claim 1, wherein each pore has a diameter ranging from approximately 10 nm to approximately 5 μm.

4. A method as recited in claim 1, wherein each pore comprises an opening extending through said membrane.

5. A method as recited in claim 1, wherein the pore comprises a pipette extending through said membrane.

6. A method as recited in claim 1, wherein each bead comprises unmodified or functionalized polystyrene.

7. A method as recited in claim 6, wherein each bead has a surface functionalized with amine or carboxyl groups to facilitate cross-linking to a terminal carboxyl or amine group, respectively, added to the terminus of nucleic acid capture probes.

8. A method as recited in claim 1, wherein said strands of capture probe nucleic acid comprise peptide nucleic acids.

9. A method as recited in claim 1, wherein the liquid comprises an electrolyte solution comprising approximately 0.01 M to approximately 1.0 M of an electrolyte in buffered water.

10. A method as recited in claim 9, wherein said electrolyte is selected from the group comprising of NaCl, KCl, and other strong electrolytes.

11. A method as recited in claim 1, further comprising:
   creating a fluid flow through said membrane from the second chamber to the first chamber, said flow generated osmotically, electroosmotically or hydrostatically.

12. A method as recited in claim 1, further comprising detecting the presence of a single nucleic acid molecule of a desired target sequence.

* * * * *